United States Patent [19]

Parker et al.

[11] Patent Number: 5,468,893

[45] Date of Patent: Nov. 21, 1995

[54] PREPARATION OF SULFUR-CONTAINING ORGANOSILICON COMPOUNDS

[75] Inventors: Dane K. Parker, Massillon; Richard T. Musleve; Robert C. Hirst, both of Akron, all of Ohio

[73] Assignee: The Goodyear Tire & Rubber Company, Akron, Ohio

[21] Appl. No.: 358,499

[22] Filed: Dec. 19, 1994

Related U.S. Application Data

[63] Continuation-in-part of Ser. No. 272,366, Jul. 19, 1994, Pat. No. 5,405,985.

[51] Int. Cl.$^6$ ........................................................ C07F 7/08
[52] U.S. Cl. ........................................................ 556/427
[58] Field of Search ............................................. 556/427

[56] References Cited

U.S. PATENT DOCUMENTS

| | | | |
|---|---|---|---|
| 3,842,111 | 10/1974 | Meyer-Simon et al. | 260/448.2 E |
| 3,873,489 | 3/1975 | Thurn et al. | 260/33.6 AQ |
| 3,978,103 | 8/1976 | Meyer-Simon et al. | 260/448.8 R |
| 3,997,581 | 12/1976 | Pietka et al. | 260/448.8 R |
| 4,129,585 | 12/1978 | Buder et al. | 260/448.8 R |
| 4,384,132 | 5/1983 | Schwarz et al. | 556/427 |
| 4,401,598 | 8/1983 | Karl et al. | 260/349 |
| 4,408,064 | 10/1983 | Schwarz et al. | 556/427 |
| 4,433,164 | 2/1984 | Jenck | 560/207 |
| 4,507,490 | 3/1985 | Panster et al. | 556/427 |
| 4,595,740 | 6/1986 | Panster | 556/427 X |
| 4,946,977 | 8/1990 | Bernhardt et al. | 556/440 |
| 5,110,969 | 5/1992 | Dittrich et al. | 556/427 |
| 5,405,985 | 4/1995 | Parker et al. | 556/427 |

FOREIGN PATENT DOCUMENTS

| | | |
|---|---|---|
| 0024926 | 8/1980 | European Pat. Off. . |
| 0029176 | 11/1980 | European Pat. Off. . |
| 0483480 | 8/1991 | European Pat. Off. . |
| 0483479 | 8/1991 | European Pat. Off. . |
| 1484909 | 9/1977 | United Kingdom . |

OTHER PUBLICATIONS

S Wolff, et al, Eur. Rubber J., 16, Jan. 1994.
K. E. Koenig, et al, Tet. Lett., 2275 (1974).
Results from a computerized technical search (1993).

*Primary Examiner*—Paul F. Shaver
*Attorney, Agent, or Firm*—Bruce J. Hendricks

[57] ABSTRACT

The present invention relates to a process for the production of organosilicon compounds of the formula $$Z-Alk-S_n-Alk-Z \qquad (I)$$

in which Z is selected from the group consisting of $$\begin{array}{ccc} R_1 & R_1 & R_2 \\ | & | & | \\ Si-R_1, & Si-R_2 \text{ and } & Si-R_2 \\ | & | & | \\ R_2 & R_2 & R_2 \end{array}$$

where $R_1$ is an alkyl group of 1 to 4 carbon atoms, cyclohexyl or phenyl;

$R_2$ is alkoxy of 1 to 8 carbon atoms, or cycloalkoxy of 5 to 8 carbon atoms;

Alk is a divalent hydrocarbon of 1 to 18 carbon atoms and n is an integer of 2 to 8; comprising reacting (A) a compound of the formula:

$$Z-Alk-X \qquad (II)$$

when X is Cl, Br or I; with (B) a compound of the formula $$Me_2S_n \qquad (III)$$

where Me is ammonium, or an alkali metal;

wherein the reaction is conducted in the presence of a phase transfer catalyst an aqueous phase and a salt of the formula $$XY \qquad (IV)$$

or $$X_2SO_4 \qquad (V)$$

where X is selected from the group consisting of Li, Na, K, Rb and Cs; and where Y is selected from the group consisting of Fl, Cl and Br.

16 Claims, No Drawings

PREPARATION OF SULFUR-CONTAINING ORGANOSILICON COMPOUNDS

This application is a continuation-in-part of U.S. Ser. No. 08/272,366 filed Jul. 8, 1994, now U.S. Pat. No. 5,405,985.

BACKGROUND

Sulfur containing organosilicon compounds are useful as reactive coupling agents between rubber and silica fillers providing for improved physical properties. They are also useful as adhesion primers for glass, metals and other substrates.

U.S. Pat. Nos. 3,842,111, 3,873,489 and 3,978,103 disclose the preparation of various sulfur containing organosilicon compounds. These organosilicon compounds are prepared by reacting (1) 2 moles of a compound of the formula

where hal is a chlorine, bromine or iodine; Z is

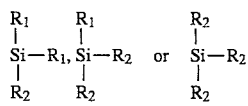

where $R_1$ is an alkyl of 1 to 4 carbon atoms or phenyl and $R_2$ is alkoxy of 1 to 8 carbon atoms; or cycloalkoxy of 5 to 8 carbon atoms; or alkylmercapto with 1 to 8 carbon atoms; Alk is a divalent aliphatic hydrocarbon or unsaturated hydrocarbon or a cyclic hydrocarbon containing 1 to 18 carbon atoms; with (2) 1 mole of a compound of the formula

where Me is ammonium or a metal atom and n is a whole number from 2 to 6. Since the two starting materials are liquid, the reaction can take place in the absence of a solvent; however, a volatile inert organic solvent is not only generally used but is preferred. The reaction is carried out with the exclusion of water. The reason for the exclusion of water is to avoid the alkaline hydrolysis reaction of the silyl alkoxy groups which will ultimately lead to insoluble polymeric by-products and lower the overall yield of desired product. Representative organic solvents include aliphatic alcohols such as methyl alcohol and ethyl alcohol. At the end of the reaction between the two starting materials, the separated salt is removed by filtration. The filtrate is then freed from the solvent by distillation under vacuum. Unfortunately, this process suffers from many practical problems. Many of these problems relate to the solvent, e.g. ethyl alcohol. Ethyl alcohol has a low flash point. In addition, it is difficult to obtain and maintain in the water-free (anhydrous) state.

SUMMARY OF THE INVENTION

The present invention relates to a process for the production of sulfur containing organosilicon compounds. The process involves reacting a haloalkylsilane compound with an ammonium polysulfide or metal polysulfide. Contrary to the previously described prior art anhydrous process, the process of the present invention is characterized by using an aqueous phase with a phase transfer catalyst.

DETAILED DESCRIPTION OF THE INVENTION

The present application is a continuation-in-part application of U.S. Ser. No. 08/272,366 filed Jul. 8, 1994, now U.S. Pat. No. 5,405,985.

There is disclosed a process for the production of organosilicon compounds of the formula

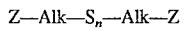  (I)

in which Z is selected from the group consisting of

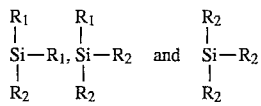

where $R_1$ is an alkyl group of 1 to 4 carbon atoms, cyclohexyl or phenyl;

$R_2$ is alkoxy of 1 to 8 carbon atoms, or cycloalkoxy of 5 to 8 carbon atoms;

Alk is a divalent hydrocarbon of 1 to 18 carbon atoms and n is an integer of 2 to 8; comprising reacting (A) a compound of the formula:

  (II)

when X is Cl, Br or I; with (B) a compound of the formula

  (III)

where Me is ammonium, or an alkali metal;

wherein the reaction is conducted in the presence of a phase transfer catalyst, an aqueous phase and a salt of the formula

  (IV)

or

  (V)

wherein X is selected from the group consisting of Li, Na, K, Rb and Cs; and wherein Y is selected from the group consisting of Fl, Cl and Br.

Examples of sulfur containing organosilicon compounds which may be prepared in accordance with the present invention include:

3,3'-bis(trimethoxysilylpropyl) disulfide,
3,3'-bis(triethoxysilylpropyl) tetrasulfide,
3,3'-bis(triethoxysilylpropyl) octasulfide,
3,3'-bis(trimethoxysilylpropyl) tetrasulfide,
2,2'-bis(triethoxysilylethyl) tetrasulfide,
3,3'-bis(trimethoxysilylpropyl) trisulfide,
3,3'-bis(triethoxysilylpropyl) trisulfide,
3,3'-bis(tributoxysilylpropyl) disulfide,
3,3'-bis(trimethoxysilylpropyl) hexasulfide,
3,3'-bis(trimethoxysilylpropyl) octasulfide,
3,3'-bis(trioctoxysilylpropyl) tetrasulfide,
3,3'-bis(trihexoxysilylpropyl) disulfide,
3,3'-bis(tri-2"-ethylhexoxysilylpropyl) trisulfide,
3,3'-bis(triisooctoxysilylpropyl) tetrasulfide,
3,3'-bis(tri-t-butoxysilylpropyl) disulfide,
2,2'-bis(methoxy diethoxy silyl ethyl) tetrasulfide,
2,2'-bis(tripropoxysilylethyl) pentasulfide,
3,3'-bis(tricyclonexoxysilylpropyl) tetrasulfide,
3,3'-bis(tricyclopentoxysilylpropyl) trisulfide,
2,2'-bis(tri-2"-methylcyclohexoxysilylethyl) tetrasulfide, bis(trimethoxysilylmethyl) tetrasulfide,
3-methoxy ethoxy propoxysilyl 3'-diethoxybutoxysilyl-propyltetrasulfide,
2,2'-bis(dimethyl methoxysilylethyl) disulfide,
2,2'-bis(dimethyl sec.butoxysilylethyl) trisulfide,
3,3'-bis(methyl butylethoxysilylpropyl) tetrasulfide,
3,3'-bis(di t-butylmethoxysilylpropyl) tetrasulfide,
2,2'-bis(phenyl methyl methoxysilylethyl) trisulfide,
3,3'-bis(diphenyl isopropoxysilylpropyl) tetrasulfide,
3,3'-bis(diphenyl cyclohexoxysilylpropyl) disulfide,
3,3'-bis(dimethyl ethylmercaptosilylpropyl) tetrasulfide,
2,2'-bis(methyl dimethoxysilylethyl) trisulfide,
2,2'-bis(methyl ethoxypropoxysilylethyl) tetrasulfide,
3,3'-bis(diethyl methoxysilylpropyl) tetrasulfide,
3,3'-bis(ethyl di-sec. butoxysilylpropyl) disulfide,
3,3'-bis(propyl diethoxysilylpropyl) disulfide,
3,3'-bis(butyl dimethoxysilylpropyl) trisulfide,
3,3'-bis(phenyl dimethoxysilylpropyl) tetrasulfide,
3-phenyl ethoxybutoxysilyl 3'-trimethoxysilylpropyl tetrasulfide,
4,4'-bis(trimethoxysilylbutyl) tetrasulfide,
6,6'-bis(triethoxysilylhexyl) tetrasulfide,
12,12'-bis(triisopropoxysilyl dodecyl) disulfide,
18,18'-bis(trimethoxysilyloctadecyl) tetrasulfide,
18,18'-bis(tripropoxysilyloctadecenyl) tetrasulfide,
4,4'-bis(trimethoxysilyl-buten-2-yl) tetrasulfide,
4,4'-bis(trimethoxysilylcyclohexylene) tetrasulfide,
5,5'-bis(dimethoxymethylsilylpentyl) trisulfide,
3,3'-bis(trimethoxysilyl-2-methylpropyl) tetrasulfide,
3,3'-bis(dimethoxyphenylsilyl-2-methylpropyl) disulfide.

The preferred sulfur containing organosilicon compounds which are prepared in accordance with the present invention are the 3,3'-bis(trimethoxy or triethoxy silylpropyl) sulfides. The most preferred compound is 3,3'-bis(triethoxysilylpropyl) tetrasulfide. Therefore as to formula I, preferably Z is

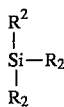

where $R_2$ is an alkoxy of 2 to 4 carbon atoms, with 2 carbon atoms being particularly preferred; Alk is a divalent hydrocarbon of 2 to 4 carbon atoms with 3 carbon atoms being particularly preferred; and n is an integer of from 3 to 5 with 4 being particularly preferred.

As to the compound of formula III, Me is ammonium or an alkali metal. Representative metals include potassium, sodium, rubidium or cesium. Preferably, Me is sodium. Specific examples of compounds of formula III include $Na_2S_2$, $K_2S_2$, $Na_2S_6$, $Cs2S_2$, $K_2S_2$, $K_2S_3$, $K_2S_2$, $(NH_4)_2S_2$, $(NH_4)_2S_3$, $Na_2S_2$, $Na_2S_3$ and $Na_2S_4$.

The process of the present invention is conducted in the presence of an aqueous phase and a salt of the formula IV or V. Representative examples of such salts include LiF, LiCl, LiBr, $Li_2SO_4$, NaF, NaCl, NaBr, $Na_2SO_4$, KF, KCl, KBr, $K_2SO_4$, RbCl, RbBr, $Rb_2SO_4$, CeCl, CeBr and $Ce_2SO_4$. Whereas the amount of salt may vary, the salt is generally present in an amount ranging from 10 percent by weight of the aqueous solution to full or complete saturation of the aqueous solution. Obviously, an excess of salt (more than full saturation) may be used; however, no additional benefit has been found. In addition, as one can appreciate, all of the various salts mentioned above have varying levels of solubility in an aqueous solution; however, the solubility of such salts are well known. In the context of saturation of the aqueous phase, it should be calculated at the desired reaction temperature since solubility of such salts in an aqueous phase are related to the temperature of the aqueous phase. Preferably, the amount of salt that is present in the aqueous phase ranges from 20 weight percent to complete or full saturation. The salt may be added to the reaction vessel at any time so long as it is present during the reaction between the compound of formula II and III. For example, the salt may be added during the formation of the compound of formula III and thereafter reacted with the compound of formula II. In the alternative, the salt of formula IV or V may be added to already formed compounds of formula III.

As mentioned above, the organosilicon compounds of formula I are prepared by reacting a compound of formula II with a compound of formula III. While the mole ratio of the two reactants may vary, generally speaking, the mole ratio of the compound of formula II to the compound of formula III ranges from about 10:1 to 1:10. Preferably the mole ratio ranges from about 4:1 to 1:4, with a range of from 2:1 being particularly preferred.

The reaction between compound of formula II and the compound of formula III is conducted in the presence of a phase transfer catalyst. Representative phase transfer catalysts may have a quaternary onium cation of the following structural formulae (VI), (VII) or (VIII):

and

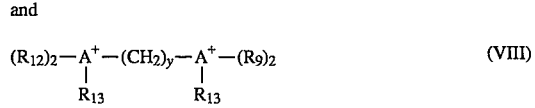

wherein A represents nitrogen, phosphorus or arsenic; $R_4$, $R_5$, $R_6$, $R_7$, which may be the same or different, are each a linear or branched chain alkyl radical containing from 1 to 16 carbon atoms, optionally substituted with a phenyl, hydroxyl, halo, nitro, alkoxy or alkoxycarbonyl substituent; a linear or branched chain alkenyl radical containing from 2 to 12 carbon atoms, preferably from 4 to 8 carbon atoms and, most preferably an alkenyl radical derived from the starting material conjugated diene; an aryl radical containing from 6 to 10 carbon atoms, optionally substituted by one or more alkyl substituents containing from 1 to 4 carbon atoms or alkoxy, alkoxycarbonyl or halo substituents; and with the proviso that any two of said radicals $R_4$ to $R_7$ may together form a single linear or branched chain alkylene, alkenylene or alkadienylene radical containing from 3 to 6 carbon atoms, $R_8$, $R_9$, $R_{10}$, $R_{11}$, which also may be the same or different, are each a linear or branched chain alkyl radical containing from 1 to 4 carbon atoms; with the proviso that the $R_{10}$ and $R_{11}$ radicals may together form an alkylene radical containing from 3 to 6 carbon atoms; and with the further proviso that the $R_9$ and $R_{10}$ or $R_9$ and $R_{11}$ radicals may together form an alkylene, alkenylene or alkadienylene radical containing 4 carbon atoms and, together with the nitrogen atom, comprising a 5-membered nitrogen heterocycle; $R_{12}$ is a linear or branched chain alkyl radical containing from 1 to 4 carbon atoms, or a phenyl radical; $R_{13}$ is a linear or branched chain alkyl radical containing from 1 to 4 carbon atoms, and which may be the same or different from $R_{12}$, a linear or branched chain alkenyl radical containing from 2 to 12 carbon atoms, preferably from 4 to 8 carbon atoms, and more preferably an alkenyl radical derived from the starting material conjugated diene to be carbonylated; and y is an integer of from 1 to 10, and preferably less than or equal to 6.

Exemplary of the quaternary onium cations having the structural Formula VI, the following are representative: tetramethylammonium, triethylmethylammonium, tributylmethylammonium, trimethyl(n-propyl)ammonium, tetraethylammonium, tetrabutylammonium, dodecyltrimethylammonium, methyltrioctylammonium, heptyltributylammonium, tetrapropylammonium, tetrapentylammonium, tetrahexylammonium, tetraheptylammonium, tetraoctylammonium, tetradecylammonium, butyltripropylammonium, methyltributylammonium, pentyltributylammonium, methyldiethylpropylammonium, ethyldimethylpropylammonium, tetradodecylammonium, tetraoctadecylammonium, hexadecyltrimethylammonium, benzyltrimethylammonium, benzyldimethylpropylammonium, benzyldimethyloctylammonium, benzyltributylammonium, benzyltriethylammonium, phenyltrimethylammonium, benzyldimethyltetradecylammonium, benzyldimethylhexadecylammonium, dimethyldiphenylammonium, methyltrialkyl($C_8$–$C_{10}$) ammonium, methyltriphenylammonium, buten-2-yltriethylammonium, N,N-dimethyltetramethyleneammonium, N,N-diethyltetramethyleneammonium, tetramethylphosphonium, tetrabutylphosphonium, ethyltrimethylphosphonium, trimethylpentylphosphonium, trimethylpentylphosphonium, octyltrimethylphosphonium, dodecyltrimethylphosphonium, trimethylphenylphosphonium, diethyldimethylphosphonium, dicyclohexyldimethylphosphonium, dimethyldiphenylphosphonium, cyclohexyltrimethylphosphonium, triethylmethylphosphonium, methyltri(isopropyl)phosphonium, methyl-tri(n-propyl)phosphonium, methyl-tri(n-butyl)phosphonium, methyl-tri(2-methylpropyl)phosphonium, methyltricyclohexylphosphonium, methyltriphenylphosphonium, methyltribenzyl phosphonium, methyl-tri(4-methylphenyl)phosphonium, methyltrixylylphosphonium, diethylmethylphenylphosphonium, dibenzylmethylphenylphosphonium, ethyltriphenylphosphonium, tetraethylphosphonium, ethyl-tri(n-propyl)phosphonium, triethylpentylphosphonium, hexadecyltributylphosphonium, ethyltriphenylphosphonium, n-butyl-tri(n-propyl)phosphonium, butyltriphenylphosphonium, benzyltriphenylphosphonium, (β-phenylethyl)dimethylphenylphosphonium, tetraphenylphosphonium, triphenyl(4-methylphenyl)phosphonium, tetrakis(hydroxymethyl)phosphonium, tetrakis(2-hydroxyethyl)phosphonium, and tetraphenylarsonium.

And exemplary of the Formula VII cations are the following: N-methylpyridinium, N-ethylpyridinium, N-hexadecylpyridinium and N-methylpicolinium.

Among the cations having the structural Formula VIII, the following are representative: 1,2-bis(trimethylammonium) ethane, 1,3-bis(trimethylammonium) propane, 1,4-bis(trimethylammonium) butane, and 1,3-bis(trimethylammonium) butane.

Representative of the anions of said onium salts include the following ions: $F^-$, $ClO_4^-$, $PF_6^-$, $BF_4^-$, tetraphenylborate anion, $PO_4^{-3}$, $HPO_4^{-2}$, $H_2PO_4^-$, $CH_3SO_3^-$, $SO_3^-$ $HSO_4^-$, $NO_3^-$, $SO_4^{-2}$, $Cl^-$, and $Br^-$. Preferably, the anion is $Cl^-$.

A particularly preferred onium salt that is used is methyl trialkyl ($C_8$–$C_{10}$) ammonium chloride which is commercially available under the trademark Adogen® 464 from Sherex Chemical Company of Dublin, Ohio, and from Henkel Corporation, Minneapolis, Minn., under the trademark Aliquot® 336.

The amount of onium salt that is used in the process of the present invention may vary. Generally speaking, the amount of onium salt will range from about 0.1 to 10 mol percent, relative to the compound of formula II, with a range of from 1 to 5 mole percent being preferred.

Wherein the phase transfer catalyst may be added to the reaction at any time, from a practical standpoint, the catalyst is preferably combined with the silane compound of formula II prior to reacting the silane compound with the sulfide compound of formula III.

The process of the present invention uses an aqueous system, however, one may optionally use a two phase aqueous/organic system. In fact, it is preferred to use an aqueous/organic system because the presence of the organic phase assists in the phase separation upon completion of the reaction. When the organic phase is used, preferably the silane compound is predissolved in the organic phase prior to addition to the sulfide compound of formula III. Representative examples of organic solvents include toluene, xylene, benzene, heptane, octane, decane, chlorobenzene and the like.

As mentioned above, the process of the present invention is conducted in the presence of an aqueous phase. The volume of water that is present may vary. Preferably, the sulfide of formula III is substantially dissolved in the aqueous phase prior to reaction with the silane compound of formula II. The concentration of the sulfide in the aqueous phase generally ranges from about 20 to 50 percent by weight. Preferably, the concentration of the sulfide in the aqueous phase ranges from about 25 to 45 percent.

In accordance with the preferred embodiment of the present invention, the sulfide of formula III is dissolved in the aqueous phase. The mixture is then heated, optionally under an inert atmosphere. The mixture may be heated to a temperature ranging from about 60° to 100° C., with a temperature of from 75° to 95° C. being preferred. The silane compound is then added to the aqueous phase. As indicated above the optional organic phase may then be added or the silane can be predissolved in the organic phase along with the appropriate amount of phase transfer catalyst. After the sulfide and silane are combined, the reaction is allowed to continue with mixing. Additional amounts of the organic solvent can then be added to further assist phase separation. Upon filtration, the filtrate is separated into the aqueous phase and organic phase containing the desired product. Any unreacted reagents and/or solvent are removed from the organic phase to yield the desired product.

This invention is illustrated by the following working example which is presented merely for the purpose of illustration and is not intended to be limiting the scope of the invention. Unless specifically indicated otherwise, parts and percentages are given by weight.

CONTROL

EXAMPLE 1

Preparation of 3,3'-bis(triethoxysilylpropyl) disulfide without salt addition

A 250 ml three necked glass reaction vessel with a mechanical stirrer and nitrogen inlet was initially charged with 20.66 g (0.086 moles) of sodium sulfide nonahydrate, 2.66 g (0.083 moles) of elemental sulfur, 20 ml of toluene and 60 ml of water. The mixture was heated with stirring under a nitrogen atmosphere to 85°–90° C. to form a homogeneous yellow-orange solution of sodium disulfide. Once formed, a solution of 40.0 g (0.166 moles) of (3-chloropropyl)triethoxysilane (CPTES) and 2.08 g (0.0045 moles) of Adogen 464 (phase transfer catalyst) was then charged into the hot sodium disulfide solution over a 10-minute period. Five minutes after the addition had been completed, the warm mixture was then filtered to remove insoluble polymer (8.0 g). The filtrate was then phase separated into a lower aqueous water solution and an upper product/toluene phase. The toluene phase was then vacuum stripped to remove excess toluene from the product. The crude product was then subjected to a high vacuum stripping to remove any. The final weight of the crude product after stripping was 22.29 g (56.7 weight percent of theory).

Proton NMR analyses was conducted to confirm the structure of the 3,3'-bis(triethoxysilylpropyl) disulfide.

CONTROL

EXAMPLE 2

Preparation of 3,3'-bis(triethoxysilylpropyl) disulfide with $Na_3PO_4 \cdot 12\ H_2O$ addition A 250 ml three necked glass reaction vessel with a mechanical stirrer and nitrogen inlet was initially charged with 20.66 g (0.086 moles) of sodium sulfide nonahydrate, 2.66 g (0.083 moles) of elemental sulfur, 20 ml of toluene, 30.0 g of $Na_3PO_4 \cdot 12\ H_2O$ (0.079 moles) and 60 ml of water. The mixture was heated with stirring under a nitrogen atmosphere to 85°–90° C. to form a homogeneous yellow-orange solution of sodium disulfide. Thereafter, a solution of 40.0 g (0.166 moles) of (3-chloropropyl)triethoxysilane (CPTES) and 2.08 g (0.0045 moles) of Adogen 464 (phase transfer catalyst) was then charged into the hot sodium disulfide solution over a 10-minute period. Five minutes after the addition had been completed, no product was produced; however, 32.0 g of insoluble polymer was formed.

EXAMPLE 3

Preparation of 3,3'-bis(triethoxysilylpropyl) disulfide with NaCl addition

A 250 ml three necked glass reaction vessel with a mechanical stirrer and nitrogen inlet was initially charged with 20.66 g (0.086 moles) of sodium sulfide nonahydrate, 2.66 g (0,083 moles) of elemental sulfur, 20 ml of toluene and 60 ml of water. The mixture was heated with stirring under a nitrogen atmosphere to 85°–90° C. to form a homogeneous yellow-orange solution of sodium disulfide. Once formed, 20.0 g (0.34 moles) of sodium chloride were added to the preformed sodium disulfide solution at 88° C. Thereafter, a solution of 40.0 g (0.166 moles) of (3-chloropropyl) triethoxysilane (CPTES) and 2.08 g (0.0045 moles) of Adogen 464 (phase transfer catalyst) was then charged into the hot sodium disulfide solution over a 10-minute period. Five minutes after the addition had been completed, the warm mixture was then filtered to remove insoluble polymer (1.129 g). The filtrate was then phase separated into a lower aqueous water-white brine solution and an upper product/toluene phase. The toluene phase was then vacuum stripped to remove excess toluene from the product. The crude product was then subjected to a high vacuum stripping to remove any. The final weight of the crude product after stripping was 25.9 g (65.9 weight percent of theory).

Proton NMR analyses was conducted to confirm the structure of the 3,3'-bis(triethoxysilylpropyl) disulfide.

EXAMPLE 4

Preparation of 3,3'-bis(triethoxysilylpropyl) disulfide with NaCl addition

A 250 ml three necked glass reaction vessel with a mechanical stirrer and nitrogen inlet was initially charged with 20.66 g (0.086 moles) of sodium sulfide nonahydrate, 2.66 g (0.083 moles) of elemental sulfur, 20 ml of toluene and 60 ml of water. The mixture was heated with stirring under a nitrogen atmosphere to 85°–90° C. to form a homogeneous yellow-orange solution of sodium disulfide. Once formed, 20.0 g (0.34 moles) of sodium chloride were added to the preformed sodium disulfide solution at 88° C. Thereafter, a solution of 40.0 g (0.166 moles) of (3-chloropropyl) triethoxysilane (CPTES) and 2.08 g (0.0045 moles) of Adogen 464 (phase transfer catalyst) was then charged into the hot sodium disulfide solution over a 10-minute period. Five minutes after the addition had been completed, the warm mixture was then filtered to remove insoluble polymer (1.78 g). The filtrate was then phase separated into a lower aqueous water-white brine solution and an upper product/toluene phase. The toluene phase was then vacuum stripped to remove excess toluene from the product. The crude product was then subjected to a high vacuum stripping to remove any. The final weight of the crude product after stripping was 25.5 g (64.9 weight percent of theory).

Proton NMR analyses was conducted to confirm the structure of the 3,3'-bis(triethoxysilylpropyl) disulfide.

EXAMPLE 5

Preparation of 3,3'-bis(triethoxysilylpropyl) disulfide with NaCl addition

A 250 ml three necked glass reaction vessel with a mechanical stirrer and nitrogen inlet was initially charged with 20.66 g (0.086 moles) of sodium sulfide nonahydrate, 2.66 g (0.083 moles) of elemental sulfur, 20 ml of toluene, 23.46 g of NaCl (0.40 moles) and 60 ml of water. The mixture was heated with stirring under a nitrogen atmosphere to 85°–90° C. to form a homogeneous yellow-orange solution of sodium disulfide. Once formed, a solution of 40.0 g (0.166 moles) of (3-chloropropyl)triethoxysilane (CPTES) and 2.08 g (0.0045 moles) of Adogen 464 (phase transfer catalyst) was then charged into the hot sodium disulfide solution over a 10-minute period. Five minutes after the addition had been completed, the warm mixture was then filtered to remove insoluble polymer (0.53 g). The filtrate was then phase separated into a lower aqueous water-white brine solution and an upper product/toluene phase. The toluene phase was then vacuum stripped to remove excess toluene from the product. The crude product was then subjected to a high vacuum stripping to remove any. The final weight of the crude product after stripping was 24.6 g (62.6 weight percent of theory).

Proton NMR analyses was conducted to confirm the structure of the 3,3'-bis(triethoxysilylpropyl) disulfide.

EXAMPLE 6

Preparation of 3,3'-bis(triethoxysilylpropyl) disulfide with NaCl addition

A 250 ml three necked glass reaction vessel with a mechanical stirrer and nitrogen inlet was initially charged with 20.66 g (0.086 moles) of sodium sulfide nonahydrate, 2.66 g (0.083 moles) of elemental sulfur, 20 ml of toluene, 30.0 g of NaCl (0.51 moles) and 60 ml of water. The mixture was heated with stirring under a nitrogen atmosphere to 85°–90° C. to form a homogeneous yellow-orange solution of sodium disulfide. Once formed, a solution of 40.0 g (0.166 moles) of (3-chloropropyl)triethoxysilane (CPTES) and 2.08 g (0.0045 moles) of Adogen 464 (phase transfer catalyst) was then charged into the hot sodium disulfide solution over a 10-minute period. Five minutes after the addition had been completed, the warm mixture was then filtered to remove only trace amounts (less than 0.1 g) of insoluble polymer. The filtrate was then phase separated into a lower aqueous water-white brine solution and an upper product/toluene phase. The toluene phase was then vacuum stripped to remove excess toluene from the product. The crude product was then subjected to a high vacuum stripping to remove any. The final weight of the crude product after stripping was 25.29 g (64.4 weight percent of theory).

Proton NMR analyses was conducted to confirm the structure of the 3,3'-bis(triethoxysilylpropyl) disulfide.

EXAMPLE 7

Preparation of 3,3'-bis(triethoxysilylpropyl) disulfide with Na$_2$SO$_4$ addition A 250 ml three necked glass reaction vessel with a mechanical stirrer and nitrogen inlet was initially charged with 20.66 g (0.086 moles) of sodium sulfide nonahydrate, 2.66 g (0.083 moles) of elemental sulfur, 20 ml of toluene, 30.0 g of Na$_2$SO$_4$ (0.21 moles) and 60 ml of water. The mixture was heated with stirring under a nitrogen atmosphere to 85°–90° C. to form a homogeneous yellow-orange solution of sodium disulfide. Once formed, a solution of 40.0 g (0.166 moles) of (3-chloropropyl)triethoxysilane (CPTES) and 2.08 g (0.0045 moles) of Adogen 464 (phase transfer catalyst) was then charged into the hot sodium disulfide solution over a 10-minute period. Five minutes after the addition had been completed, the warm mixture was then filtered to remove insoluble polymer (1.8 g). The filtrate was then phase separated into a lower aqueous water solution and an upper product/toluene phase. The toluene phase was then vacuum stripped to remove excess toluene from the product. The crude product was then subjected to a high vacuum stripping to remove any. The final weight of the crude product after stripping was 29.4 g (74.8 weight percent of theory).

Proton NMR analyses was conducted to confirm the structure of the 3,3'-bis(triethoxysilylpropyl) disulfide.

EXAMPLE 8

Preparation of 3,3'-bis(triethoxysilylpropyl) tetrasulfide with NaCl addition

A 250 ml three necked glass reaction vessel with a mechanical stirrer and nitrogen inlet was initially charged with 20.66 g (0.086 moles) of sodium sulfide nonahydrate, 8.18 g (0.255 moles) of elemental sulfur, 20 ml of toluene, 30.0 g of NaCl (0.51 moles) and 60 ml of water. The mixture was heated with stirring under a nitrogen atmosphere to 85°–90° C. to form a homogeneous yellow-orange solution of sodium tetrasulfide. Once formed, a solution of 40.0 g (0.166 moles) of (3-chloropropyl)triethoxysilane (CPTES) and 2.08 g (0.0045 moles) of Adogen 464 (phase transfer catalyst) was then charged into the hot sodium tetrasulfide solution over a 10-minute period. Five minutes after the addition had been completed, the warm mixture was then filtered and no insoluble polymer was detected. The filtrate was then phase separated into a lower aqueous water-white solution and an upper product/toluene phase. The toluene phase was then vacuum stripped to remove excess toluene from the product. The crude product was then subjected to a high vacuum stripping to remove any. The final weight of the crude product after stripping was 36.7 g (82.3 weight percent of theory).

Proton NMR analyses was conducted to confirm the structure of the 3,3'-bis(triethoxysilylpropyl) tetrasulfide.

What is claimed is:

1. A process for the production of organosilicon compounds of the formula

$$Z-Alk-S_n-Alk-Z \qquad (I)$$

in which Z is selected from the group consisting of

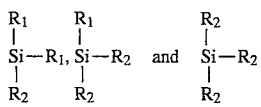

where R$_1$ is an alkyl group of 1 to 4 carbon atoms, cyclohexyl or phenyl;

R$_2$ is alkoxy of 1 to 8 carbon atoms, or cycloalkoxy of 5 to 8 carbon atoms;

Alk is a divalent hydrocarbon of 1 to 18 carbon atoms and n is an integer of 2 to 8; comprising reacting (A) a compound of the formula:

$$Z-Alk-X \qquad (II)$$

when X is Cl, Br or I; with (B) a compound of the formula

$$Me_2S_n \qquad (III)$$

where Me is ammonium, or an alkali metal;

wherein the reaction is conducted in the presence of a phase transfer catalyst, an aqueous phase and a salt of one of the following formulae

$$XY \qquad (IV)$$

or

$$X_2SO_4 \qquad (V)$$

wherein X is selected from the group consisting of Li, Na, K, Rb and Cs; and wherein Y is selected from the group consisting of Fl, Cl and Br.

2. The process of claim 1 wherein Z is:

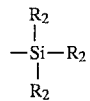

R$_2$ is an alkoxy of 2 to 4 carbon atoms, n is an integer of from 2 to 4, and Alk is a divalent hydrocarbon of 2 to 4 carbon atoms.

3. The process of claim 1 wherein X is Cl.

4. The process of claim 1 wherein Me is sodium.

5. The process of claim 2 wherein R is an alkoxy of 2 carbon atoms.

6. The process of claim 1 wherein the reaction is carried out at a temperature ranging from 60° C. to 100° C.

7. The process of claim 1 wherein the reaction is conducted in the presence of an aqueous phase and an organic phase.

8. The process of claim 1 wherein the phase transfer catalyst is selected from formulae:

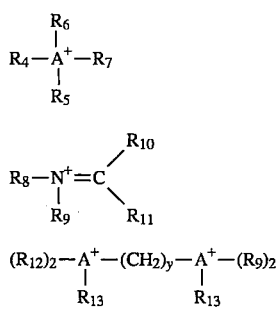

wherein A represents nitrogen, phosphorus or arsenic; $R_4$, $R_5$, $R_6$, $R_7$, which may be the same or different, are each a linear or branched chain alkyl radical containing from 1 to 16 carbon atoms, may be substituted with a phenyl, hydroxyl, halo, nitro, alkoxy or alkoxycarbonyl substituent; a linear or branched chain alkenyl radical containing from 2 to 12 carbon atoms; an aryl radical containing from 6 to 10 carbon atoms, may be substituted by one or more alkyl substituents containing from 1 to 4 carbon atoms or alkoxy, alkoxycarbonyl or halo substituents; and with the proviso that any two of said radicals $R_4$ to $R_7$ may together form a single linear or branched chain alkylene, alkenylene or alkadienylene radical containing from 3 to 6 carbon atoms, $R_8$, $R_9$, $R_{10}$, $R_{11}$, which also may be the same or different, are each a linear or branched chain alkyl radical containing from 1 to 4 carbon atoms; with the proviso that the $R_{10}$, and $R_{11}$ radicals may together form an alkylene radical containing from 3 to 6 carbon atoms; and with the further proviso that the $R_9$ and $R_{10}$ or $R_9$ and $R_{11}$ radicals may together form an alkylene, alkenylene or alkadienylene radical containing 4 carbon atoms and, together with the nitrogen atom, comprising a 5-membered nitrogen heterocycle; $R_{12}$ is a linear or branched chain alkyl radical containing from 1 to 4 carbon atoms, or a phenyl radical; $R_{13}$ is a linear or branched chain alkyl radical containing from 1 to 4 carbon atoms, and which may be the same or different from $R_{12}$, a linear or branched chain alkenyl radical containing from 2 to 12 carbon atoms; and y is an integer greater than or equal to 1 and less than or equal to 10.

9. The process of claim 8 wherein said phase transfer catalyst is selected from the group of cations consisting of tetramethylammonium, triethylmethylammonium, tributylmethylammonium, trimethyl(n-propyl)ammonium, tetraethylammonium, tetrabutylammonium, dodecyltrimethylammonium, methyltrioctylammonium, heptyltributylammonium, tetrapropylammonium, tetrapentylammonium, tetrahexylammonium, tetraheptylammonium, tetraoctylammonium, tetradecylammonium, butyltripropylammonium, methyltributylammonium, pentyltributylammonium, methyldiethylpropylammonium, ethyldimethylpropylammonium, tetradodecylammonium, tetraoctadecylammonium, hexadecyltrimethylammonium, benzyltrimethylammonium, benzyldimethylpropylammonium, benzyldimethyloctylammonium, benzyltributylammonium, benzyltriethylammonium, phenyltrimethylammonium, benzyldimethyltetradecylammonium, benzyldimethylhexadecylammonium, dimethyldiphenylammonium, methyltrialkyl($C_8$–$C_{10}$) ammonium, methyltriphenylammonium, buten-2-yltriethylammonium, N,N-dimethyltetramethyleneammonium, N,N-diethyltetramethyleneammonium, tetramethylphosphonium, tetrabutylphosphonium, ethyltrimethylphosphonium, trimethylpentylphosphonium, trimethylpentylphosphonium, octyltrimethylphosphonium, dodecyltrimethylphosphonium, trimethylphenylphosphonium, diethyldimethylphosphonium, dicyclohexyldimethylphosphonium, dimethyldiphenylphosphonium, cyclohexyltrimethylphosphonium, triethylmethylphosphonium, methyl-tri(isopropyl)phosphonium, methyl-tri(n-propyl)phosphonium, methyl-tri(n-butyl)phosphonium, methyl-tri(2-methylpropyl)phosphonium, methyltricyclohexylphosphonium, methyltriphenylphosphonium, methyltribenzyl phosphonium, methyl-tri(4-methylphenyl)phosphonium, methyltrixylylphosphonium, diethylmethylphenylphosphonium, dibenzylmethylphenylphosphonium, ethyltriphenylphosphonium, tetraethylphosphonium, ethyl-tri(n-propyl)phosphonium, triethylpentylphosphonium, hexadecyltributylphosphonium, ethyltriphenylphosphonium, n-butyl-tri(n-propyl)phosphonium, butyltriphenylphosphonium, benzyltriphenylphosphonium, (β-phenylethyl)dimethylphenylphosphonium, tetraphenylphosphonium, triphenyl(4-methylphenyl)phosphonium, tetrakis(hydroxymethyl)phosphonium, tetrakis(2-hydroxyethyl)phosphonium, tetraphenylarsonium, N-methylpyridinium, N-ethylpyridinium, N-hexadecylpyridinium, N-methylpicolinium, 1,3-bis-2-yldimethylammonium) propane, 1,2-bis(trimethylammonium)ethane, 1,3-bis(trimethylammonium)propane, 1,4-bis(trimethylammonium)butane, and 1,3-bis(trimethylammonium)butane and selected from the group of anions consisting of $F^-$, $ClO_4^-$, $PF_6^-$, $BF_4^-$, tetraphenylborate anion, $PO_4^{-3}$, $HPO_4^{-2}$, $H_2PO_4^-$, $CH_3SO_3^-$, $SO_3^-$, $HSO_4^-$, $NO_3^-$, $SO_4^{-2}$, $Cl^-$, and $Br^-$.

10. The process of claim 1 wherein said phase transfer catalyst is methyl trialkyl ($C_8$–$C_{10}$) ammonium chloride.

11. The process of claim 1 wherein said phase transfer catalyst is an onium salt that is present in an amount ranging from 0.1 to 10 mol percent relative to the compound of formula II.

12. The process of claim 7 wherein an organic solvent is selected from the group consisting of toluene, xylene, benzene, heptane, octane, decane, chlorobenzene and the like.

13. The process of claim 12 wherein said organic solvent is toluene.

14. The process of claim 1 wherein said salt is NaCl.

15. The process of claim 1 wherein said salt is present in an amount ranging from 10 weight percent of the aqueous solution to full saturation of the aqueous solution.

16. The process of claim 1 wherein said salt is present in an amount ranging from 20 weight percent of the aqueous to full saturation of the aqueous solution.

* * * * *